| United States Patent [19] | [11] Patent Number: 4,919,149 |
|---|---|
| Stang | [45] Date of Patent: Apr. 24, 1990 |

[54] CONTRACEPTION AND FLAVOR DELIVERY SYSTEM

[76] Inventor: Michael A. Stang, 26 Stockmill Rd., Apt. F, Pikesville, Md. 21208

[21] Appl. No.: 216,351

[22] Filed: Jul. 8, 1988

[51] Int. Cl.⁵ .......................... A61F 5/00; A61F 5/42; A61F 5/44

[52] U.S. Cl. .................................. 128/842; 128/844; 128/79; 604/349

[58] Field of Search ................. 128/842, 843, 844, 79; 604/347–353, 330; 206/69; 2/408

[56] References Cited

U.S. PATENT DOCUMENTS

| 2,586,674 | 2/1952 | Lonne | 604/349 |
|---|---|---|---|
| 3,486,507 | 12/1969 | Bregenzer | 2/408 |
| 3,536,066 | 10/1970 | Ludwig | 128/842 |
| 3,659,599 | 5/1972 | McLaughlin | 604/349 |
| 3,809,090 | 5/1974 | Poulacs | 604/347 |
| 4,432,357 | 2/1984 | Pomeranz | 604/349 |
| 4,807,611 | 2/1989 | Johnson | 604/349 |
| 4,820,290 | 4/1989 | Yahr | 604/353 |

*Primary Examiner*—Robert A. Hafer
*Assistant Examiner*—Michael Brown
*Attorney, Agent, or Firm*—Morton J. Rosenberg; David I. Klein

[57] ABSTRACT

A contraception and flavor delivery system (10) includes an extended tubular member (20) having a closed distal end (22) and an open proximal end (24). The contraception and delivery system (10) further includes a mechanism for flavor delivery (30) formed on an external surface of the tubular member (20). The mechanism for flavor delivery (30) includes at least one longitudinally extended tubular housing (40) having an open first end (42) and a closed second end (46) for containing a predetermined quantity of an ingestible flavored composition. The open first end (42) of tubular housing (40) is provided with a closure (44) adapted to release the ingestible flavored composition into a bodily orifice responsive to an external stimuli.

18 Claims, 2 Drawing Sheets

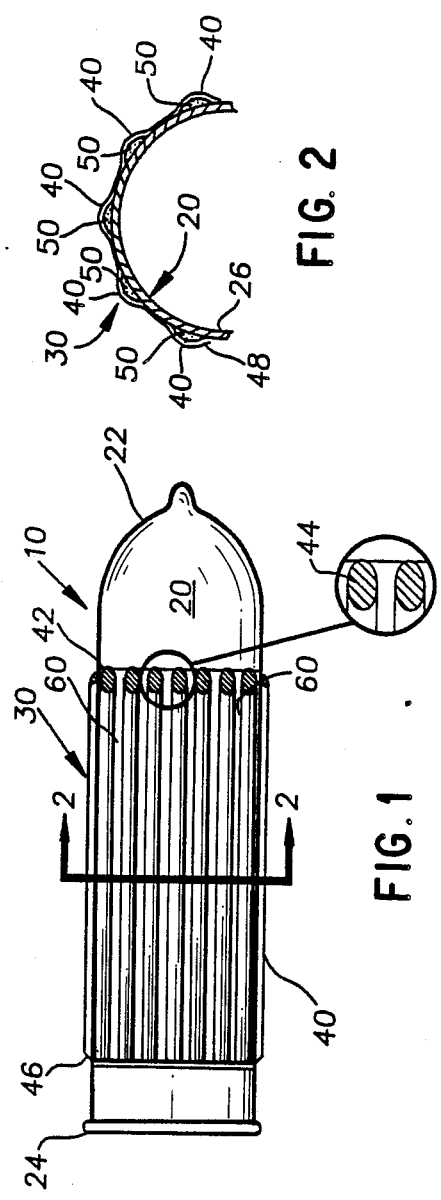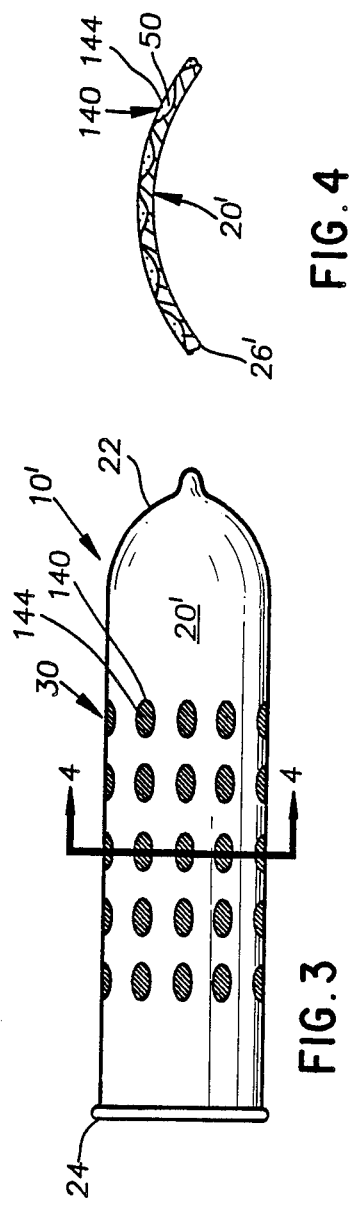

CONTRACEPTION AND FLAVOR DELIVERY SYSTEM

BACKGROUND OF THE INVENTION

1. Field of the Invention

This invention directs itself to contraceptive systems for preventing the transmittal of disease and preventing conception. In particular, this invention directs itself to a condom-like device which includes a means for dispensing a flavored composition into the bodily orifice penetrated therewith. More in particular, this invention pertains to condom-like devices having at least one tubular housing formed on an external surface thereof for containing a predetermined quantity of an ingestible flavored composition. Further, this invention directs itself to a means for delivering a flavored composition to a bodily orifice having a closure adapted to release the flavored composition responsive to an external stimuli.

2. Prior Art

Contraceptive systems are well known in the art. The best prior art known to the Applicant include U.S. Pat. Nos.: 4,432,357; 4,498,466; 4,564,006; 4,508,114; 3,809,090; 4,009,717; and, 4,625,718, and include the publication entitled "The Condom Book" by Jane Everett and Walter D. Glanze, Copyright 1987.

In some prior art systems, such as that described in the publication entitled "The Condom Book" condom-like devices formed from a confection, known as candy condoms, are provided. The device which is sleeve-shaped is placed over the male genital member and while playful penetration is possible, the device is intended to be simply eaten off. However, this device does not offer any contraceptive protection, nor does it provide any protection from the transmittal of disease.

In other prior art systems, such as U.S. Pat. Nos. 4,432,357; 4,498,466; and, 4,564,006, there are provided condoms having at least one sealed chamber formed on at least a portion of the external surface of the tubular sheath. The outer layer is heat sealed to the inner sheath-like member to form a plurality of chambers which are fluid filled. However, the fluid with which these chambers are filled is a rheopexic fluid, increasing in consistency responsive to increasing sheer stress provided by frictional forces applied thereto. In these systems the fluid remains within the chambers and is not released responsive to an external stimuli, as provided by the instant invention.

In other prior art systems such as described in U.S. Pat. No. 4,508,114, there are provided antirape devices having a condom-like construction to be worn within the vaginal cavity of a female. Located within the condom-like tubular member is formed a housing for containing a liquid. The housing is frangible and intended to dispense the liquid, a skin irritant, upon forceful contact by a penetrating penis. Thus, these systems do not dispense an ingestible flavored composition from a housing formed on an external surface of the tubular member, which serves to prevent transmittal of disease and prevents conception, as provided by the instant invention.

SUMMARY OF THE INVENTION

A contraception and flavor delivery system includes a prophylactic element for at least partial insertion into a bodily orifice defining an extended tubular member. The tubular member has a closed distal end and an open proximal end for encompassing at least a portion of a male genital member. The contraception and flavor delivery system further includes a means for flavor delivery formed on an external surface of the tubular member. The means for flavor delivery is adapted for dispensing an ingestible composition having a predetermined taste into a bodily orifice.

BRIEF DESCRIPTION OF THE DRAWINGS

FIG. 1 is a plane view of the contraceptive system;

FIG. 2 is a partial sectional view of the contraceptive system taken along the section line 2—2 of FIG. 1;

FIG. 3 is a plane view of an alternate embodiment of the contraceptive system;

FIG. 4 is a partial sectional view of the contraceptive system taken along the section line 4—4 of FIG. 3;

DESCRIPTION OF THE PREFERRED EMBODIMENTS

Figure 5:
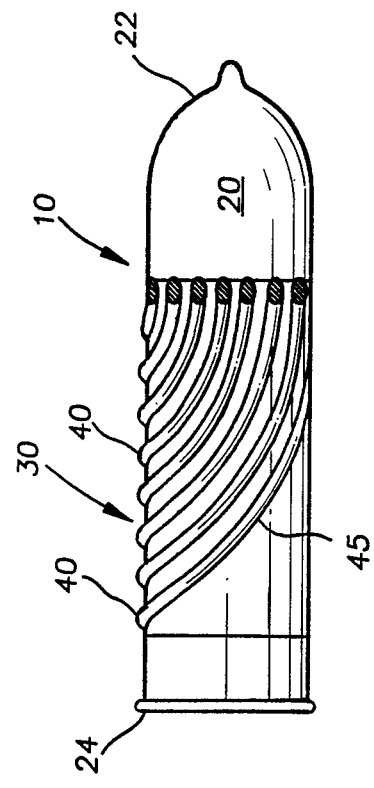
FIG. 5 is a plane view of an alternate embodiment for the contraceptive system shown in FIG. 1; and, FIG. 6 is another alternate embodiment of the contraceptive system of FIG. 1.

Referring now to FIGS. 1 and 2, there is shown contraception and flavor delivery system 10 for preventing the transmittal of disease between sexual partners, preventing conception, and releasing an ingestible composition having a predetermined taste into a bodily orifice. As will be seen in following paragraphs, contraception and flavor delivery system 10 is specifically directed to the concept of providing a system for releasing the pleasantly flavored ingestible composition 50 responsive to an external stimuli. In addition to adding to sexual enjoyment through the release of a pleasantly flavored composition, contraception and flavor delivery system 10 is constructed such that the means for flavor delivery 30 is formed by a plurality of raised projections 40 for increasing physical pleasure during sexual intercourse.

Contraception and flavor delivery system 10 includes a prophylactic member 20 defined by a tubular member having a closed distal end 22 and an open proximal end 24. Prophylactic member 20 is defined by a tubular wall 26 formed from latex or similar material compositions, as is well known in the art. Thus, prophylactic member 20 is much like other commercially available prophylactic devices for use by a male to prevent conception and the transmittal of disease. However, contraception and flavor delivery system 10 includes a means for delivering a flavored composition to a bodily orifice coupled to an external surface of prophylactic member 20.

The means for flavor delivery 30 includes one or more tubules 40 coupled to the external surface of the tubular wall 26 of prophylactic member 20. The tubules 40 extend longitudinally from an open first end, located adjacent the distal closed end 22 of prophylactic member 20, to a closed second end located adjacent the open proximal end 24 of prophylactic member 20. Each of tubules 40 contain a predetermined quantity of an ingestible flavored composition for release to a bodily orifice responsive to an external stimuli, as will be described in following paragraphs.

The tubules 40 are formed by a tubular wall 48 having an undulating cross-sectional configuration which is bonded to the external surface of the prophylactic member's tubular wall 26 on three surrounding sides of each tubule 40. Thus, between each tubule 40 there is a portion 60 of wall 48 which is bonded to the external surface of tubular wall 26. The tubules 40 are closed at second end 46 by a similar bonding technique, which may be provided by means of adhesive, solvent, or heat. The tubules thus formed are filled with a substantially viscous flavored ingestible composition through the open ends 42 of tubules 40. Subsequent to being filled with a predetermined quantity of the flavored composition 50 each of the tubules is sealed by a closure 44.

Closure 44 is designed to maintain the flavored composition 50 within tubule 40 until such time that an external stimuli triggers its release. In one embodiment, closure 44 is formed by a frangible member bonded to each tubule 40 for releasing the flavored composition 50 responsive to a predetermined frictional force which causes closure 44 to rupture. The frangible closure 44 may be formed by a thin latex or plastic film-like sheet, which is easily ruptured by the frictional forces applied to contraceptive and flavor delivery system 10 during sexual activity.

In an alternate embodiment, closure 44 is formed by a sealing member which changes from a solid to a liquid state responsive to an external stimuli. Thus, closure 44 may be formed by a composition which changes from a solid to a liquid responsive to exposure to a predetermined temperature. Such closures may be formed by a glycerine composition, as is well known in the pharmacological art, which melt when exposed to ambient temperatures substantially equivalent to human body temperature, for release of the flavored composition 50. Alternately, closure 44 could be formed by a confection which melts, or dissolves, responsive to exposure to a liquid, present in the bodily orifice, such as saliva.

Once the opening in tubule 40 sealed by closure 44 has been opened, the flavored composition 50 will be dispensed. However, flavored composition 50 being substantially viscous, does not readily flow from the tubules 40. Flavored composition 50 will be slowly aspirated from tubules 40 by the frictional forces which are applied to contraception and flavor delivery system 10 during sexual intercourse. When contraception and flavor delivery system 10 is used in conjunction with oral stimulation, the flavored composition 50 is dispensed by suction and the frictional forces that are applied to tubules 40 during such activity.

The tubules 40 provide a non-smooth exterior surface for prophylactic member 20, even when all of the flavored composition 50 has been expelled, and thereby increases the frictional contact between contraceptive system 10 and the vaginal cavity into which it is introduced during sexual intercourse. The increased frictional contact has the additional benefit of contributing to the physical pleasure derived therefrom.

Referring now to FIGS. 3 and 4, there is shown an alternate embodiment of the contraceptive and flavor delivery system 10' having a contraceptive member 20' wherein means for flavor delivery 30 is formed therein. The means for flavor delivery 30 being provided by one or more recesses, or pockets formed in the wall 26' of prophylactic member 20'. The pockets 140 formed in tubular wall 26' may extend partially into the wall thickness of tubular wall 26', or alternatively, the pockets 140 may be formed by inwardly directed projections of wall 26' which extend at least partially into the interior of prophylactic member 20'(not shown). Such extension of portions of wall 26' into the interior of prophylactic member 20' provides an additional advantage for the contraceptive system 10 in aiding the retention of the tubular member 20' on the penis of the user.

Each of the recesses 140 formed in the wall 26' of prophylactic member 20' is filled with a predetermined quantity of the flavored ingestible composition 50. Subsequently, the recesses 140 containing the flavored composition 50 are provided with a closure 144, as was previously described for the embodiment of FIG. 1 and 2. Each of the recesses 140 may be fitted with an individual closure 144 or a single closure encompassing all of the recesses 140 can be applied to the prophylactic member 20'.

As has been previously described, contraception and flavor delivery system 10 includes a tubular prophylactic member 20 which functions to prevent the transmittal of disease and further functions to prevent conception, as is similarly provided by commercially available condom like devices. In addition, contraceptive and flavor delivery system 10 is provided with a means for flavor delivery 30 coupled to the external surface of prophylactic member 20 adding a new facet to the sexual activity with which condoms are used.

Means for flavor delivery 30, as shown in FIGS. 1 and 2, is formed by at least one tubule 40 having an open first end 42 and a closed second end 46. Tubule 40 is formed by a tubular wall 48 having an undulating cross-sectional configuration, with raised portions forming the tubules 40 which extend adjacent the portions 60. The portions 60 are bonded to the tubular wall 26 of prophylactic member 20. The closed second end 46 of the tubule 40 is similarly bonded to the tubular wall 26 of prophylactic member 20, adjacent the proximal open end 24 of prophylactic member 20. The tubules 40 thus formed, provide a housing for containing the flavored ingestible composition 50 of predetermined viscosity.

Each of the tubules 40 are provided with a closure 44 which is designed to release the flavored composition 50 responsive to an external stimuli. When closure 44 is formed by a frangible seal, the flavored composition 50 is released to a bodily orifice responsive to frictional force applied to the tubular housings 40. Closure 44 can also be formed from a material composition which changes state from a solid to a liquid for release of the flavored composition 50 to the bodily orifice into which it penetrates during sexual activity. Thus closure 44 may be formed of a composition which melts at substantially body temperature to release the flavored composition subsequent to intimate contact with the body of the user's sexual partner. Alternatively, closure 44 can be formed by a composition which dissolves in the presence of a liquid solvent, such as saliva. For providing release of the flavored composition 50 during oral stimulation.

Additionally, the raised projections formed by tubular housings 40 provide an additional physical stimulating effect, in that they add a fluted contour to the external surface of the prophylactic member 20 for increasing frictional contact. As will be discussed in following paragraphs, the fluted contour of the means for flavor delivery 30 can be provided in alternate configurations to further enhance the physical stimulation derived therefrom.

As an alternate means of delivering the flavored composition 50 to a bodily orifice with a condom-like member, prophylactic member 20' is provided with one or more recessed portions 140 formed in the tubular wall 26' of the prophylactic member 20'. Each of the recessed portions 140 extend at least partially into the wall 26' for holding a predetermined quantity of the flavored composition 50. The recessed portions 140 are provided with a closure 144 having characteristics virtually the same as those for closure 40 of the embodiment previously discussed. However, recesses 140 may be filled with a confectionery composition which is solidified at room ambient temperature, and therefore would not require the closure 144. The solid confectionery composition would of course be soluble in the presence of saliva to provide a pleasantly flavored taste to the outer surface of contraceptive system 10.

Referring now to FIG. 5, there is shown an alternate to the embodiment of FIGS. 1 and 2. In this embodiment, the tubular housings 40 are formed in a helical pattern about the longitudinal axis of the prophylactic member 20. Thus, each of the tubular housings 40 are provided with at least one arcuate portion 45 located intermediate the open first end and closed second end of housing 40.

This helical arrangement of tubular housings 40 provides an angular component to the raised projections formed by housings 40. The angular component thus provided has the effect of increasing the physical stimulation provided by the raised projection formed by housings 40. Further, the serpentine configuration of each tubular housing 40 requires greater frictional or suction forces to be applied thereto for extracting the flavored composition contained therein.

Figure 6:
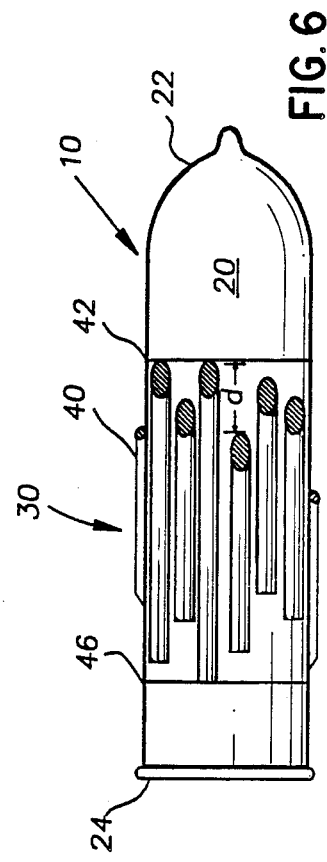

As shown in FIG. 6, there is provided an alternate embodiment for contraception and flavor delivery system 10 wherein the means for flavor delivery 30 is formed by a plurality of longitudinally staggered tubular housings 40. In this embodiment, the tubular housings 40 are each arranged such that consecutive tubular housings are staggered in a longitudinal direction. Thus, each adjacent tubular housing is longitudinally displaced by a variable predetermined distance d. This staggered arrangement provides release of the flavored composition incrementally as a function of the depth of penetration. Additionally, the staggered arrangement of the raised projections formed by the housings 40 add still another variation to the physical stimulation provided thereby.

It is to be understood that the flavoring composition as herein described may be one or more of a number of well-known ingestible flavoring compositions 50. Such well-known prior art flavoring compositions may be chocolate, corn syrup, or one or combinations of numerous well-known synthetic ingestible flavoring compositions acceptable for ingestion into the human body.

It is to be further understood that the flavoring composition having particular delivery means as herein described may be coatings formed external to the prophylactic element. Such provisions as coatings would constitute the flavor delivery mechanism formed on the external surface of the tubular members as herein described.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed all without departing from the spirit or scope of the invention as defined in the appended claims.

What is claimed is:

1. A contraception and flavor delivery system, comprising:
    a prophylactic element for at least partial insertion into a bodily orifice defining an extended tubular member, said tubular member having a closed distal end and an open proximal end for encompassing at least a portion of a male genital member; and,
    flavor delivery means formed on an external surface of said tubular member, said flavor delivery means adapted for dispensing an ingestible composition having a predetermined taste into said bodily orifice, said flavor delivery means including at least one tubular housing formed on said tubular member having an open first end and a closed second end, said tubular housing including closure means coupled to said open first end for releasing said ingestible composition responsive to an external stimuli.

2. The contraception and flavor delivery system as recited in claim 1 wherein said flavor delivery system includes closure means coupled to said open first end of said tubular housing for releasing said ingestible composition responsive to an external stimuli.

3. The contraception and flavor delivery system as recited in claim 2 wherein said closure means includes a frangible member for releasing said ingestible composition responsive to a predetermined frictional force being applied thereto.

4. The contraception and flavor delivery system as recited in claim 2 wherein said closure means includes a sealing member having a solid first state and a liquid second state.

5. The contraception and flavor delivery system as recited in claim 4 wherein said sealing member changes state and thereby releases said ingestible composition responsive to a predetermined temperature.

6. The contraception and flavor delivery system as recited in claim 4 wherein said sealing member changes state and thereby releases said ingestible composition responsive to a solvent found in said bodily orifice.

7. The contraception and flavor delivery system as recited in claim 1 wherein said flavor delivery means includes a plurality of tubular housings, each of said tubular housings extend longitudinally from an open first end to a closed second end for containing a predetermined quantity of said ingestible composition.

8. The contraception and flavor delivery system as recited in claim 7 wherein said plurality of tubular housings are formed coaxially about a perimeter portion of said tubular member.

9. The contraception and flavor delivery system as recited in claim 8 wherein said first and second ends of said plurality of tubular housings are longitudinally aligned each with respect to the other.

10. The contraception and flavor delivery system as recited in claim 8 wherein said plurality of tubular housings are arranged with consecutive tubular housings being staggered in a longitudinal direction.

11. The contraception and flavor delivery system as recited in claim 8 wherein each of said plurality of tubular housings extend helically from said first end to said second end in parallel relationship each with respect to the other.

12. The contraception and flavor delivery system as recited in claim 7 wherein said flavor delivery system includes closure means coupled to said open first end of each said tubular housing for releasing said ingestible composition responsive to an external stimuli.

13. The contraception and flavor delivery system as recited in claim 12 wherein said closure means includes a frangible member for releasing said ingestible composition responsive to a predetermined frictional force being applied thereto.

14. The contraception and flavor delivery system as recited in claim 12 wherein said closure means includes a sealing member having a solid first state and a liquid second state.

15. The contraception and flavor delivery system as recited in claim 14 wherein said sealing member changes state and thereby releases said ingestible composition responsive to a predetermined temperature.

16. The contraception and flavor delivery system as recited in claim 14 wherein said sealing member changes state and thereby releases said ingestible composition responsive to a solvent found in said bodily orifice.

17. The contraception and flavor delivery system as recited in claim 1 wherein said flavor delivery means includes at least one recess formed in a wall of said tubular member for containing said ingestible composition.

18. The contraception and flavor delivery system as recited in claim 17 wherein said flavor delivery means includes closure means for releasing said ingestible composition responsive to an external stimuli, said closure means overlaying said recess.

* * * * *